US010930373B2

(12) United States Patent
Majumdar et al.

(10) Patent No.: US 10,930,373 B2
(45) Date of Patent: Feb. 23, 2021

(54) METHODS AND SYSTEMS FOR KNOWLEDGE DISCOVERY USING BIOLOGICAL DATA

(71) Applicant: LIFE TECHNOLOGIES CORPORATION, Carlsbad, CA (US)

(72) Inventors: Nivedita Sumi Majumdar, San Bruno, CA (US); Harrison Leong, San Francisco, CA (US); Shakila Pothini, Union City, CA (US); David Hoard, Escondido, CA (US); Christopher Fong, Pleasanton, CA (US); Pratik Simon Soares, Foster City, CA (US); Salil Kumar, Princeton, NJ (US); Thomas Wessel, Pleasanton, CA (US); Manjula Aliminati, Santa Clara, CA (US); Levente Egry, Sunnyvale, CA (US)

(73) Assignee: Life Technologies Corporation, Carlsbad, CA (US)

( * ) Notice: Subject to any disclaimer, the term of this patent is extended or adjusted under 35 U.S.C. 154(b) by 44 days.

(21) Appl. No.: 15/128,859

(22) PCT Filed: Mar. 24, 2015

(86) PCT No.: PCT/US2015/022298
§ 371 (c)(1),
(2) Date: Sep. 23, 2016

(87) PCT Pub. No.: WO2015/148546
PCT Pub. Date: Oct. 1, 2015

(65) Prior Publication Data
US 2017/0177792 A1    Jun. 22, 2017

Related U.S. Application Data

(60) Provisional application No. 62/073,925, filed on Oct. 31, 2014, provisional application No. 61/969,749, filed on Mar. 24, 2014.

(51) Int. Cl.
*G16B 50/00*    (2019.01)
*G16B 30/00*    (2019.01)
(Continued)

(52) U.S. Cl.
CPC ............ *G16B 50/00* (2019.02); *G06F 16/904* (2019.01); *G06F 16/951* (2019.01); *G16B 30/00* (2019.02); *G16B 45/00* (2019.02)

(58) Field of Classification Search
CPC .......... G06F 19/26; G06F 19/28; G06F 19/22; G06F 16/904
See application file for complete search history.

(56) References Cited

U.S. PATENT DOCUMENTS

2003/0032069 A1* 2/2003 Muraca .................. G06F 19/28
                                                      435/7.21
2004/0019432 A1  1/2004 Sawafta et al.
(Continued)

OTHER PUBLICATIONS

Huang, H. et al., "Using IBM Content Manager for Genomic Data Annotation and Quality Assurance Tasks", *IBM Journal of Research and Development*, vol. 55, No. 6, 2011, 1-18.
(Continued)

*Primary Examiner* — William Spieler
(74) *Attorney, Agent, or Firm* — François A. Pelaez

(57) ABSTRACT

A system for analyzing biological data, comprising: a storage configured to store a plurality of data files containing biological data obtained from a plurality of devices; a server configured to: host a plurality of applications, each configured to be implemented on the server and to provide analysis, manipulation, comparison, visualization, or a combination thereof, of the biological data included in the data files, wherein the plurality of applications allow a user to analyze different data files related to the same sample and compare the results of the analysis.

19 Claims, 17 Drawing Sheets

(51) Int. Cl.
*G16B 45/00* (2019.01)
*G06F 16/904* (2019.01)
*G06F 16/951* (2019.01)

(56) References Cited

U.S. PATENT DOCUMENTS

| | | | |
|---|---|---|---|
| 2007/0043694 A1 | 2/2007 | Sawafta et al. | |
| 2010/0318528 A1 | 12/2010 | Kupershmidt et al. | |
| 2011/0292072 A1* | 12/2011 | Fisher .................... | G06T 11/60 |
| | | | 345/619 |
| 2014/0186309 A1* | 7/2014 | Klassen ................. | A61K 35/30 |
| | | | 424/93.7 |
| 2016/0203188 A1* | 7/2016 | O'Connor ........... | G06F 11/3476 |
| | | | 707/756 |

OTHER PUBLICATIONS

International Application No. PCT/US2015/022298, International Search Report and Written Opinion dated Jun. 9, 2015, 14 pages.
Podpecan, V. et al., "Orange4WS Environment for Service-Oriented Data Mining", *The Computer Journal*, vol. 55, No. 1, Aug. 2011, 1-18.

* cited by examiner

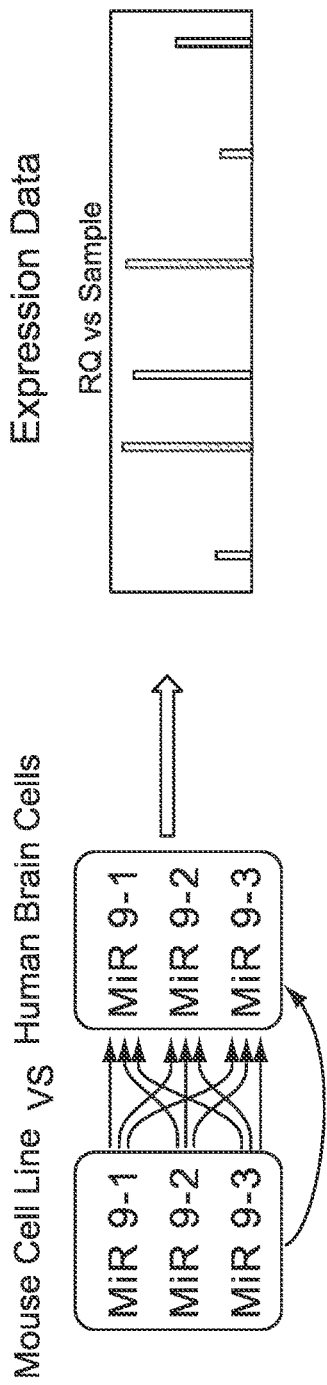
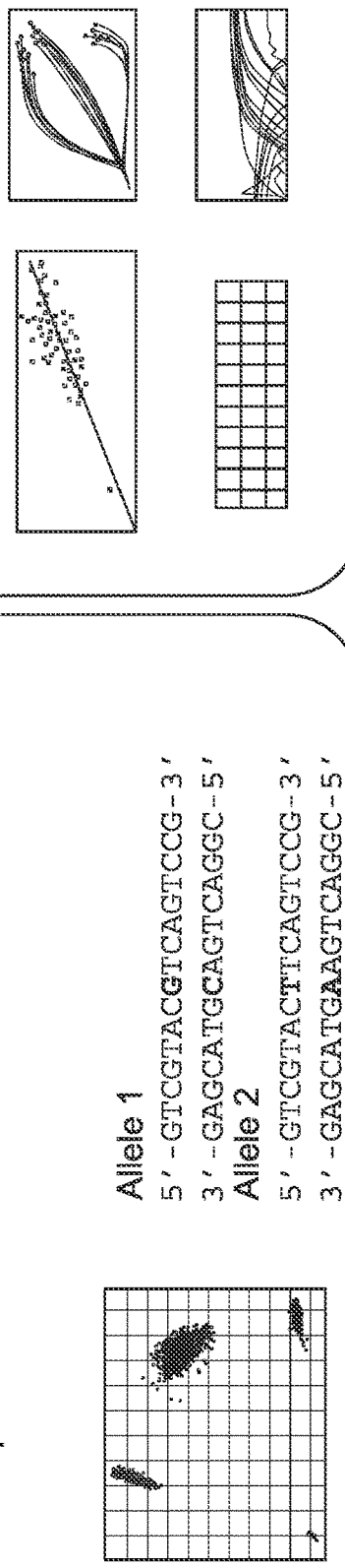
FIG. 11

FIG. 12

Project: PCR_Drug_discovery_108bt

Manage Data

| ☐ File | Plate Barcode | Block type | Instrument | # of wells | Date run |
|---|---|---|---|---|---|
| ☐ NT51_2012_12_04_112736.eds | INT51 | Open Array | QuantStudio 12K Flex | 3072 | 2012/12/4 |
| ☐ NT51_2012_12_04_112736.eds | INT51 | Open Array | Viia 7 | 96 | 2012/12/4 |
| ☐ NT51_2012_12_04_112736.eds | INT51 | Open Array | ABI 7900 | 3072 | 2012/12/4 |
| ☐ NT51_2012_12_04_112736.eds | INT51 | Open Array | QuantStudio 12K Flex | 384 | 2012/12/4 |
| ☐ NT51_2012_12_04_112736.eds | INT51 | Open Array | Viia 7 | 96 | 2012/12/4 |
| ☐ NT51_2012_12_04_112736.eds | INT51 | Open Array | ABI 7900 | 3072 | 2012/12/4 |
| ☐ NT51_2012_12_04_112736.eds | INT51 | Open Array | ABI 7900 | 3072 | 2012/12/4 |

Delete selected — Import from local drive — Import from Digital Hub

METHODS AND SYSTEMS FOR KNOWLEDGE DISCOVERY USING BIOLOGICAL DATA

BACKGROUND

Conventional systems for analyzing biological data comprise some type of device or modality that is configured to obtain the biological data. This data can then often be collected and analyzed by some form of computer application or applications. In such conventional systems, such applications are typically loaded onto a local computer and the data is stored in a local memory. Consequently, such applications typically are configured to run on specific hardware, have limited capacity, and allow limited access. Moreover, in such conventional systems, a different application is needed for each type of data, which requires the user to go back and forth between applications to look at different types of data.

It should be clear, therefore, that the ability to cross correlate data, perform quality assurance checks, detect patters in the data, look at large amounts of data, provide stream lined work flows, etc., is limited in such conventional systems. A biological study typically involves gathering and comparing various sets of biological data. While such conventional systems and applications have made such studies far easier, the limitations noted above require the user to manually compare various types of biological data and the full potential or promise of such applications cannot fully be recognized due to such system limitations.

For example, a user may run various qPCR-based experiments to gather distinct types of biological data, such as genotyping data or gene expression data, about a gene of interest to the study. The user may also run sequencing experiments. If the user wants to compare data for a particular sample or target across these various types of data sets, then the user would have to manually move between applications to find data related to, e.g., the same sample and then manually analyze or compare these data sets. Thus, combining and corroborating, getting deeper detail, discovering new biological links and understanding emergent patterns is left mainly up to the researcher to accomplish with entirely manual workflows. This is painstaking, error-prone, and really limiting in today's world of information deluge.

SUMMARY

Methods and systems for a server-based system configured to allow analysis of a plurality of biological data files within a single workspace are described herein.

According to one aspect, a system for analyzing biological data, comprises a storage configured to store information related to a plurality of data files containing biological data obtained from a plurality of devices; a server configured to: host a plurality of applications, each configured to be implemented on the server and to provide analysis, manipulation, comparison, visualization, or a combination thereof, of the biological data included in the data files, create tags associated with the information included in the plurality of data files and store the tags in the storage; and a search engine configured to enable the tags to be search and build associations between the tags.

According to another aspect, a system for analyzing biological data, comprises a storage configured to store a plurality of data files containing biological data obtained from a plurality of devices; a server configured to: create tags associated with the information included in the plurality of data files and store the tags in the storage, and host a plurality of applications, wherein at least some of the plurality of applications includes at least on of visualization modules, analysis modules, and quality control modules, and wherein the modules are linked with the data based on the tags enabling a user to drill down through the data in the data files or move from one module to the next and review information related to the same data or data files within the different modules.

According to another aspect, a system for analyzing biological data, comprises a storage configured to store a plurality of data files containing biological data obtained from a plurality of devices; a server configured to: host a plurality of applications, each configured to be implemented on the server and to provide analysis, manipulation, comparison, visualization, or a combination thereof, of the biological data included in the data files, wherein the plurality of applications allow a user to analyze different data files related to the same sample and compare the results of the analysis.

In certain embodiments, a system for analyzing biological data, comprises a storage configured to store a plurality of data files containing biological data obtained from a plurality of devices, wherein the data files content including measurement data and meta data is used to automatically or manually associate data files to one another to produce distinct groupings that are appropriate for a plurality of applications, each configured to be implemented on the server and to provide analysis, manipulation, comparison, visualization, or a combination thereof, of the biological data included in the data files, wherein the plurality of applications allow a user to analyze different data files related to the same sample and compare the results of the analysis. For example, it would be desirable to search and or group or associate files with the same target or sequence. Furthermore, not only can the file content be used but external or internal tags can also be used. As in some cases, a file can be tagged with metadata for any purpose where the tag information is held external to the file with the association of the tag to the file being maintained by another software component. The tag information may also be held in the file.

In another embodiment, a system for analyzing biological data, comprises a storage configured to store a plurality of data files containing biological data obtained from a plurality of devices from different sources. In particular, sources can be but not limited to different people or users or members, different laboratories, different institutions, different companies, different countries, different computer systems or different instruments. As such, a plurality of applications, each configured to be implemented on the server and to provide analysis, manipulation, comparison, visualization, or a combination thereof, of the biological data included in the data files, wherein the plurality of applications allow a user to analyze different data files related to the same characteristic by which the data files have been grouped or associated across the various sources. This embodiment allows users to share data with other users. It also allows users to make discoveries not possible with their own data alone. The system would host applications that would enable collaboration between sources by analyzing data grouped from different sources. These applications would analyze the data with algorithms such as, but not limited to machine learning, pattern recognition, and use data transformations including Fourier transforms, Eigen decompositions.

Trend analysis that can be provided through an application hosted on the server as described can provide tremendous value. A highly valuable research tool is the ability to track trends in the data or meta data. In a clinical setting for instance, it is vital to detect when a patient's data deviates substantially from a steady state mode. The system can have algorithms to detect this through a variety of algorithmic flags and filters.

The systems and methods described herein allow management of the data files for quick and efficient searches. One such procedure is to index the data by the various tags, meta data or measurement data; however, the large volume of data may make this impractical. Another such procedure would be to compress the information first and perform analysis of the information in its compressed form. Indexing, searching and analysis can be done on the compressed information without the need to uncompress the data first. This reduces the computational load to perform the equivalent computation on the uncompressed data.

One skilled in the art would recognize the need for paging technologies. To enable quick response time in the user interface, the backend server must adaptively and preemptively load data files that might be needed. In the system, there are different types of storage and each form of storage has a different degree of latency to queries and requests. Therefore, the associations and grouping by tags, metadata or measurement data enable the system to reload associated data files before the user requests them or needs them.

Furthermore, as data is required to be displayed it may become necessary to perform various methods for caching the data and providing a sliding window of data. As the user progresses through the data, the sliding window changes bringing in new data. The cache is updated with new data as and when the sliding window moves. The sliding window data is cached at various granularity levels. The method includes storing a first portion of the data at a first granularity level and a second portion at a second granularity level. The data is cached at various granularity levels in order to effectively use the cache considering at least cache updating criteria A collaborative networking system as described herein presents a user with automated analysis of tags, metadata and measurement data. In particular, the collaborative networking system provides a pre-fetched set of data files to a user device of the viewing user and a presentation of the analysis that led to the data file associations.

Navigating on a display includes tracking motion of an input tool on a display, comparing a motion of the input tool to a threshold, and changing a position of the visible portion of a plot of information on the display if the input tool motion exceeds the threshold. The position of the visible portion of the page of information on the display is constrained if the motion does not exceed the threshold.

A system as described herein for obtaining metrics for online advertising uses multiple sources of user data, including panel data, collaborative networking system data, and the tags, metadata and measurement data contained internally or externally to the data files. An advertising algorithm system identifies appropriate advertising based on a user demographics report.

To switch between applications efficiently and quickly, one method includes providing a plurality of thumbnails for display on a display device, receiving an indication that a user selected a particular thumbnail, and providing one or more instructions to change from data content that the user is currently analyzing to data content associated with the particular thumbnail. Each of the plurality of thumbnails includes a visual indication representing data content previously viewed by the user. The plurality of thumbnails are operable to change from data content that the user is currently watching to data content corresponding to the particular thumbnail selected by the user.

DESCRIPTION OF THE FIGURES

FIG. 11 illustrates yet another example of comparing a plurality of biological data types according to various embodiments described herein;

FIG. 12 illustrates an exemplary user interface dashboard to view available biological data according to various embodiments described herein;

FIG. 13 illustrates an exemplary user interface a user may use to add biological data to the system according to various embodiments described herein; and FIG. 14 illustrates an exemplary user interface display showing various applications a user may use to analyze biological data according to various embodiments described herein.

DETAILED DESCRIPTION

To provide a more thorough understanding of various embodiments, the following description sets forth numerous specific details, such as specific configurations, parameters, examples, and the like. It should be recognized, however, that such description is not intended to limit the embodiments described to specific implementations, configurations, etc. Nor do the descriptions necessarily provide complete descriptions of the embodiments. As such, certain aspects, features, components, etc., may be omitted from the description of the various embodiments for ease of explanation.

In the systems and methods described herein, a user can obtain data from a plurality of devices or modalities, analyze the data, create a plurality of various visualizations of the data, cross correlate the data, launch various applications to view, analyze or manipulate the data all from within a single platform and interface. Examples of types of biological data that can be collected include, but are not limited to, technology vectors, biological molecule vectors, and the output data of various applications configured to work on these vectors. Examples of technological vectors can include, but are not limited to, CE sequencing, NGS sequencing, qPCR, dPCR, melt, microArrays, and combinations thereof. Examples of biological molecule vectors include, but are not limited to DNA, RNA, proteins, miRNA, etc. Examples of applications that produce output data based on these vectors include, but are not necessarily limited to genotyping applications, gene expression applications, absolute quantification applications, Copy Number Variation (CNV) analysis applications, Single Nucleotide Polymorphism (SNP) array analysis applications, High Resolution Melt (HRM) analysis applications, presence-absence analysis applications, etc. Thus, the outputs of these applications would also be biological data that can be used with the systems and methods described herein. Other information that can be consider biological data are meta-data, such as data that indicates disease information or treatment outcomes can also be used with the systems and methods described herein.

Figure 6:
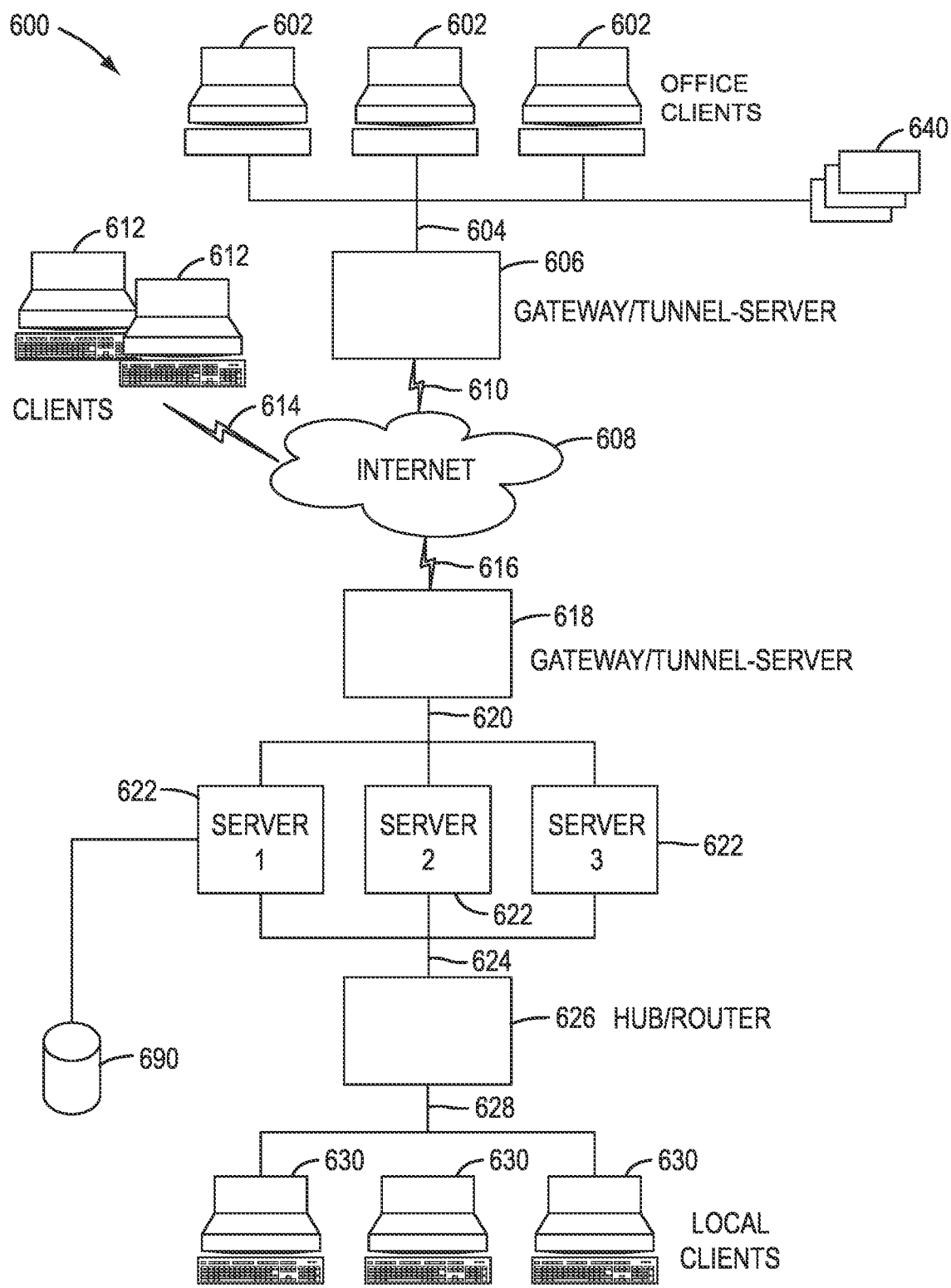
FIG. 6 illustrates an exemplary distributed network system according to various embodiments described herein.
Figure 7:
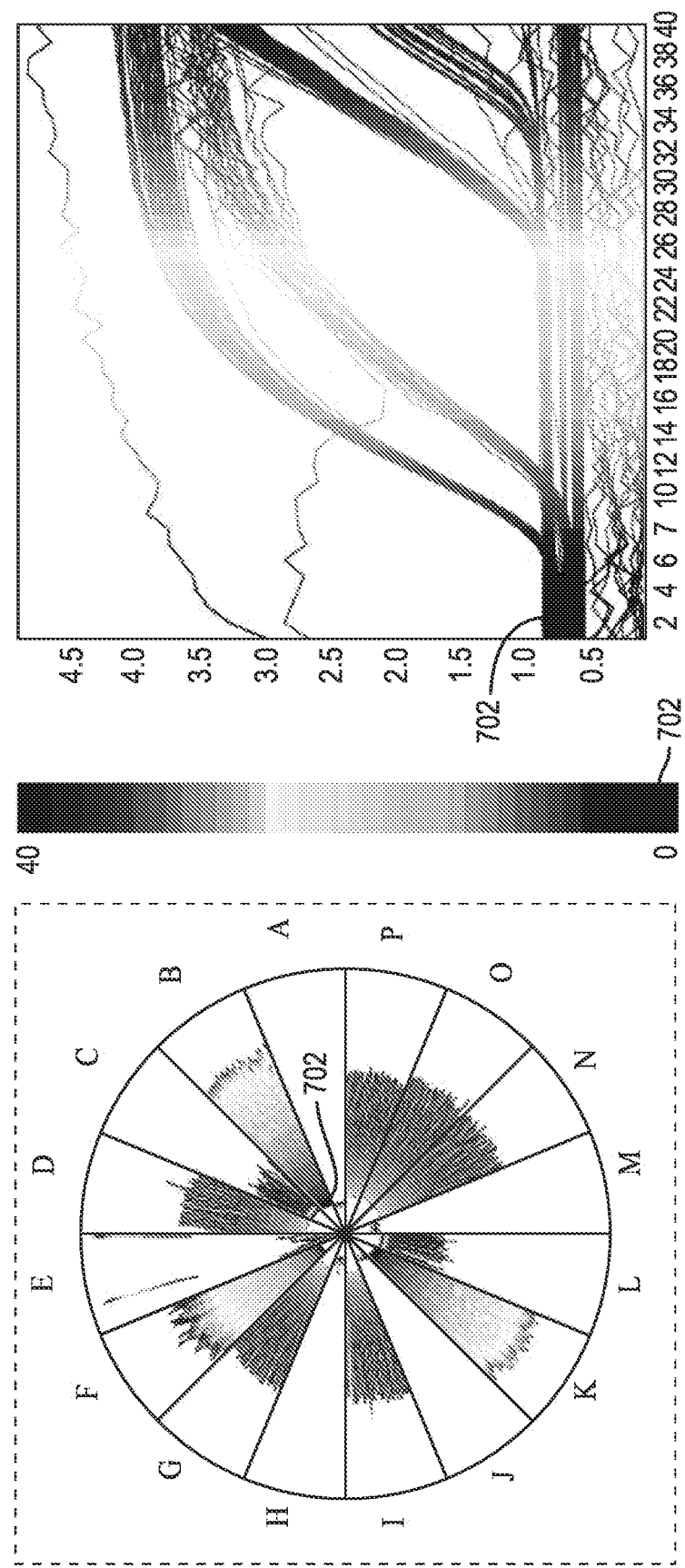
FIG. 7 illustrates an exemplary data visualization display for biological data according to various embodiments described herein.

FIG. 6 is a diagram illustrating an example system 600 configured in accordance with one example embodiment. In system 600, one or more servers 622 can be configured to run the analysis applications for analyzing data sets produced by one or more devices or modalities 640. The data included in the data sets can be stored in one or more storage devices 650. Once the data sets have been uploaded to servers 622, then a plurality of applications running on servers 622 can be used to manipulate, analyze and visualize the data sets from anywhere. For example, local client devices 630 can be used to access servers 622, e.g., through a hub or router 626. At the same time, the data can be accessed remotely through remote clients devices 602, which are interfaced with servers 622, e.g., via a gateway/hub/tunnel-server/etc. 610, which is itself connected to the internet 608 via some internet service provider (ISP) connection 610, or remote client servers 612, which are interfaced with servers 622, e.g., via the internet 608 and via an ISP connection 614.

Thus, a user can simply activate a browser program resident on clients 602, 612, or 630 in order to access the platform and applications running on servers 622. In certain embodiments, the browser can then present a user interface (see FIG. 1A) that can include a dash board in which all of the user's data, devices, samples, targets, visualizations, etc., can be displayed an access in a convenient format.

Figure 12:
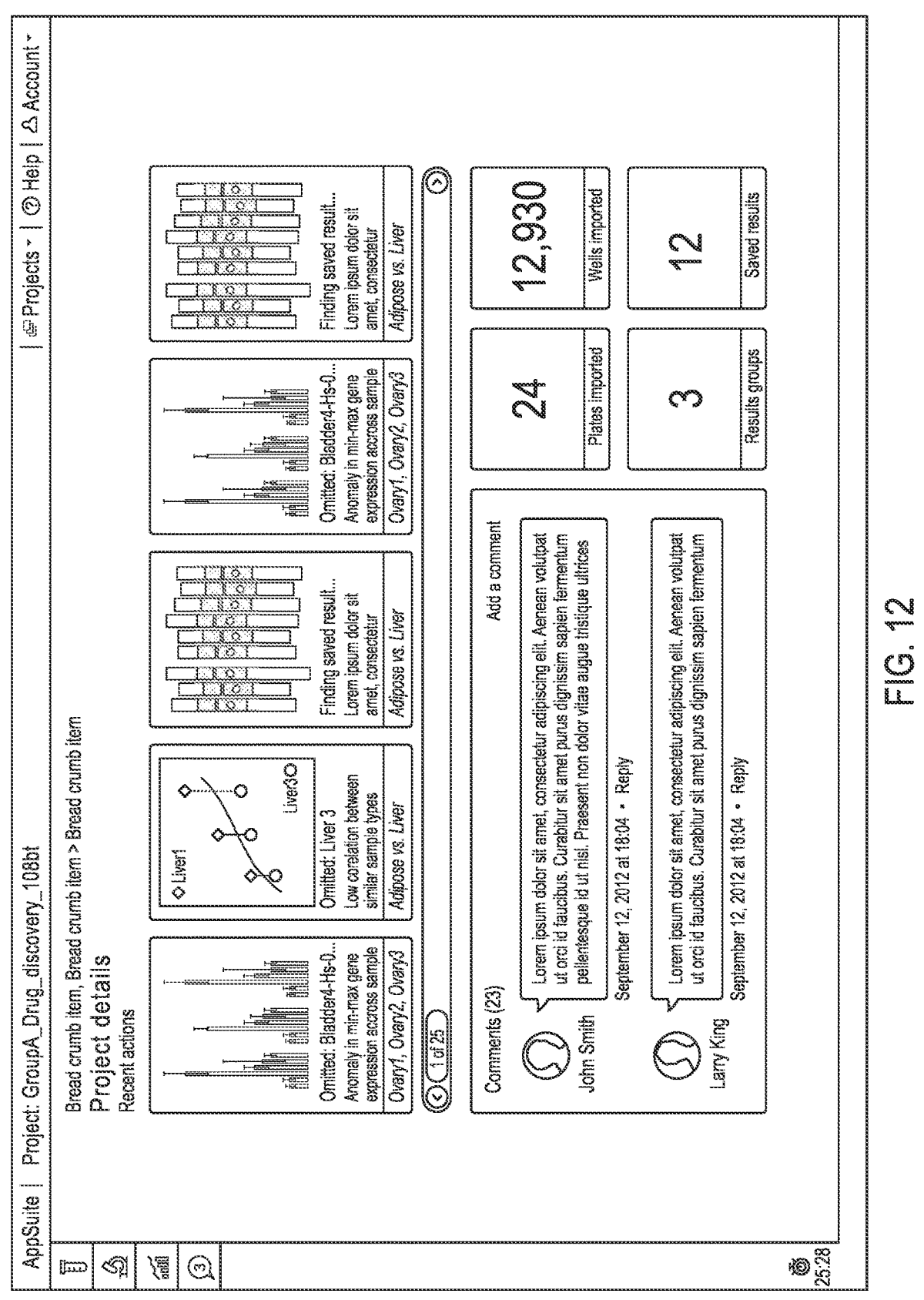
Figure 14:
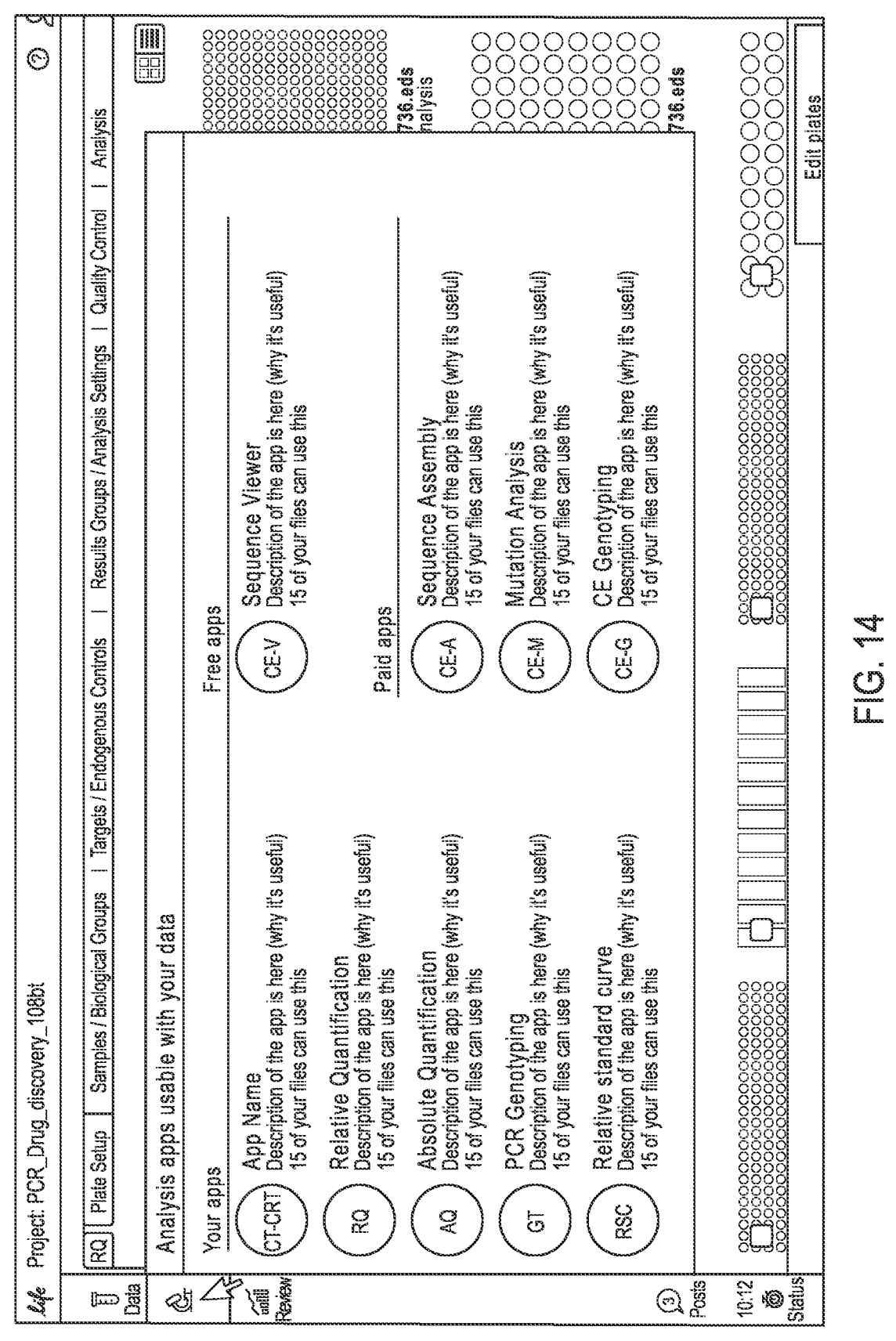

FIGS. 12-14 illustrated example screen shots of an exemplary dash board in accordance with certain embodiments. As can be seen in FIG. 12, information related to a certain project can be displayed with the dashboard. This information can include recent actions, information on the plates and wells from which data was imported, the number of groups created, the number of results saved, as well as comments from various collaborators on the project. It should also be noted that data from experiments performed by other users can also be imported into the user's workspace or dashboard.

Along the left in this example, are tabs that allow the user to go to the corresponding data, applications, visualizations, etc. Thus, if the user selects the data tab as illustrated in FIG. 13, then information on the various files can be displayed. As noted, the user can use the system to search in a complex fashion as described below.

As noted, users can collaborate. To enable this, in certain embodiments, the data manager maintains a list of users associated with a project. The list can include one or more owners, who can have deletion rights. Every user with "rights" to a project can have both read and write access, or only read access. For example, the access privileges can be based on the role of the user and the intended purpose of the study. For example, in a core lab setup, there are technicians and scientists and principal investigators that may require differing access privileges to the same project. In certain embodiments, others are locked out once the project is marked "in-use" by any one of the shared users. But in other embodiments, concurrent data review is possible.

It should be noted that while only files are illustrated in FIG. 13, the system can also store projects, which are groups of files. Thus, the user can search for and select a project, which will pull up the files only related to that project. The applications related to those files can then automatically be highlighted or otherwise indicated as described below.

Selection of the applications tab will then highlight all of the applications that can be used with the files as illustrated in FIG. 14. The user can then launch any of the applications from within the dashboard and then pull up any of the data that can viewed with that application. It should also be noted that system 600 can act as an application store allowing users to purchase applications, download applications for free, download, or upload their own applications etc. This can allow further development, even by third parties, of applications that can act on the common types of data sets stored with in system 600.

It should also be noted that devices 640 can be directly interfaced with servers 622, e.g., through the internet. In such embodiments, the collection application and functionality can reside on servers 622, on devices 640, or both. In other embodiments, devices 640 can be interfaced with client devices 602 or 612. In such embodiments, the collection application or functionality can be included on client devices 602 or 612, devices 640, or both.

Client devices 602, 612, and 630 can be any kind of computing device that can be used to access servers 622. As such, these devices can be laptop, desktop, or palmtop computers, terminals, mobile computing devices such as smartphones or tablets, etc. Servers 622 can comprise one or more processors, servers, routers, co-processors, user interfaces, etc., whether co-located or located in different locations. In short, servers 622 can comprise all of the resources, both hardware and software, needed to perform the functions described herein. A more detailed description of a computer system and the resources that can be used to implement the components illustrated in FIG. 6 is described below with respect to FIG. 5.

Figure 1A:
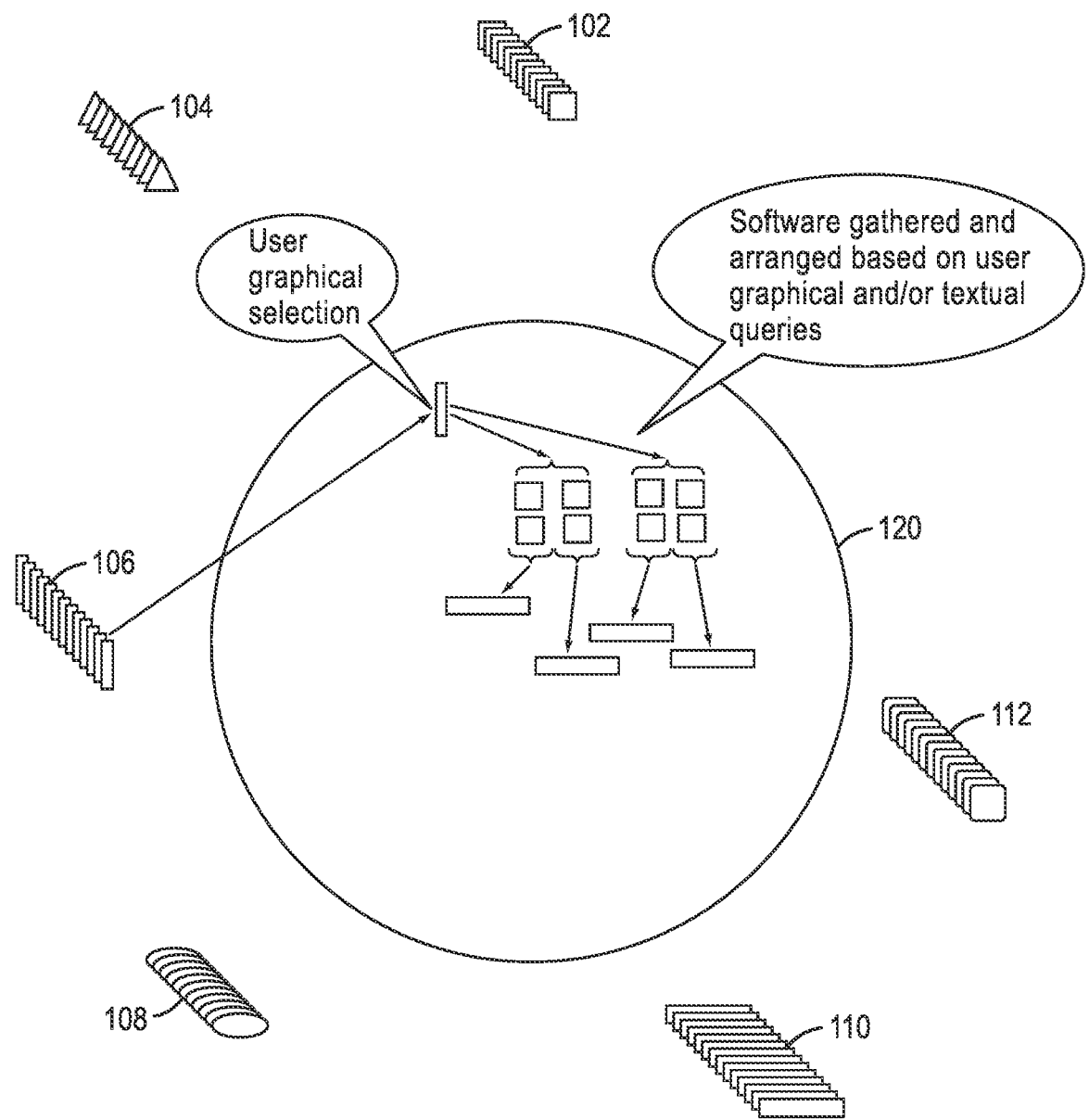
FIG. 1A illustrates an exemplary system according to various embodiments described herein.

FIG. 1A is a diagram illustrating an example user interface that can be included in system 600 in accordance with one embodiment. As noted above, various data files can be uploaded from devices 640. Thus, various types of data files can be uploaded to servers 622 and, e.g., stored in storage 650. For example, data files 102 are of a first biological type, data files 104 are of a second biological type, data files 106 are of a third biological type, data files 108 are of a fourth biological type, data files 110 are of a fifth biological type, and data files 112 are of a sixth biological type.

Currently, biological instruments and associated software applications enable a user to determine biological results from data acquired from different biological instruments. For example, sequences are determined from electropherograms and Cq values from amplification data. But in conventional systems, the applications are proprietary, run on local client devices, e.g., devices 602, have limited storage and are dedicated to one type of data often only for certain types of analyses.

Using the systems and methods described herein, however, the user can upload data files from a plurality of devices 640 into one platform and create a workspace or project in which the user can use a plurality of applications to access these data files, cross reference data points in the various data files, look across studies, search by data, instrument, sample, target, sequence, assay, visualization, etc. Thus, the challenge of manually bringing all of the researcher's data together into one workspace, allowing cross analysis based upon sample names, biological sequences and any other user defined tags and meta-data to capture themes user wishes to study together can be provided. For example, the embodiments described herein can allow user to not only connect among the different qPCR applications such as genotyping and gene expression, it can also enable cross analysis between, e.g., sequencing and qPCR. It will further enable querying and linkage to the large biological information databases, helping users to understand their phenomenon of interest in the larger biological context. Thus, questions like determining the cause of a certain cancer, a relationship of genetic heredity to diseases, the efficacy of drugs, or the effectiveness of a therapy may be easier to analyze and answer using embodiments of the present teachings.

In certain embodiments, this ability to look across data sets, cross reference, access multiple applications, etc., is at least partially enabled due to a linking of the various data sets to the applications that can be used to view that data. Thus, for example, in the dashboard the user can see all of their data, instrument, sample, target, sequence, assay, visualization, etc. When the user selects a data file, the corresponding applications can then be highlighted so the user knows what applications can be used for a given file. The user can then launch an application to view, analyze or manipulate the data. In certain embodiments, the user can tag or annotate the data in one application. This tag or annotation can be stored with the underlying data. When the user pulls up that data in a different application, the tag or annotation information can still be associated with the same data point in the data generated by that particular application.

In general, the applications, e.g., as illustrated in FIG. 14, as well as the visualization tools, analysis tools, manipulation tools, etc., within the application are link to the underlying data files, e.g., as illustrated in FIG. 13. This linkage with the data allows a user to pull up the data in an application, analyze the data, create visualization of the data or the analysis, and easily drill down to see details with respect to, e.g., certain sample or targets, pull up visualizations or analysis of the, e.g., samples or targets, perform quality review of the data, and provide simultaneous access to multiple applications.

In certain embodiments, this linkage is enabled because all of the information, content, attributes, etc., within the data can be used as indexes or tags that can then be used to build a non-relational database based on the indexes or tags. This type of non-relational database built from all of the data files can enable powerful functionality including machine learning capabilities and search capabilities which are described in detail below. But it also allows this linkage to the application level that enables the functions described above. For example, the system will automatically identify the type of data included in a data file, based on attributes associated with the data, the data file, or both, and automatically associated the data or data file with the applications that can act on that data.

For example, in certain embodiments, when the user pulls up the data as illustrated in FIG. 13, the applications that can act on the data can appear, e.g., on the left side of the screen. This association of the data to the applications is done based on the analysis of the type of data file. For example, for qPCR data, the user may have available the Relative Quantification (RQ) and Absolutely Quantification (AQ) applications, e.g., with their subscription. Thus, the user can alternatively or simultaneously pull up the RQ and AQ applications and perform analysis of certain data.

For example, if the user where to launch the RQ application, the user could then cross-correlate quality information by sample name by supporting navigation to different graphics within the RQ application. The user can also move from, e.g., a RQ plot or volcano plot within the RQ application to amplification plots, which can allow the user to, e.g., review the underlying data quality. Further, the user can pull up the actual scatter plot from the correlation matrix heat maps based upon which the correlation is calculated. The user can also bookmark samples and move between the quality review area and results presentation area in genotyping. The user can also have bookmarked data selected out specifically for export. The user can also annotate samples in one file in one application and have that information available for the same sample in another application.

In certain embodiments, enhanced quality review is provided wherein, e.g., the user can move between the quality flags and results area, visualize quality flags overlaid on the results, to instantly get feedback on data quality, have an overall "status" flag available per well that uses sophisticated shape assessment to call out poor quality wells.

The user can also, for example, review and compare biological data acquired from different technologies. For example, according to various embodiments, a user may review and compare PCR data with Capillary Electrophoresis (CE) data. A user may review data related to the same sample or sequence to confirm or corroborate a SNP result. Further, these capabilities can be used, for example, to provide an indication of data or sample quality. For example, by using data from two different qPCR technologies, such as genotyping and gene expression data, a user may be able to determine if a point in a genotyping cluster plot is a copy number variation or is a poor quality sample. By using the gene expression or genotyping data, a user can confirm the quality level of the samples.

Complex data interpretation is also provided. For example, within the RQ application, interactive heat maps can provide swift assessment of overall patterns, a histogram driven sorter can provide quick ability to zero in on curves of interest in high volume data scenarios. For the GT application, the ability to see the real-time traces on an allelic discrimination plot allows the user to choose the cycle number for best cluster separation and also troubleshoot the results in situations with copy number variations.

As an example, in FIG. 14, if the user launches the RQ application, then various tabs, or options can become available. In of these tabs can allow the user to access the plate setup. The plate setup is automatically linked to the underlying data. Accordingly, the user can actually switch the plate view from, e.g., task to target to sample as desired. A view of the plates and wells will then correspondingly show information, e.g., in a color coded format for the task, target, or sample by well. Clicking on or hovering over a well can then pull up information for the task, target or sample associated with the well. The user can then select, or deselect certain, e.g., wells or targets for inclusion in further analysis, in the plate setup tab or in other tabs.

A groups tab can allow the user to create biological groups as well as analysis groups. For example, the user can group certain related biological data into a biological group for further analysis. But the user can also select different biological groups into an analysis group for further analysis. This can allow the user to select a control or change the control for the various groups included in the analysis group for example.

A data review tab can be used to pull up the primary output for the data included for analysis, e.g., the amplification plots. The user can then omit certain wells, add wells, etc. If a user selects a certain well or plot, then a detailed data view can be presented that can be filtered based on various parameters. Again, because the parameters of the underlying data are tagged and linked to the applications and the modules within the applications, this advanced functionality that allows drill down, filtering, search, etc., within the applications is enabled.

Figure 9:
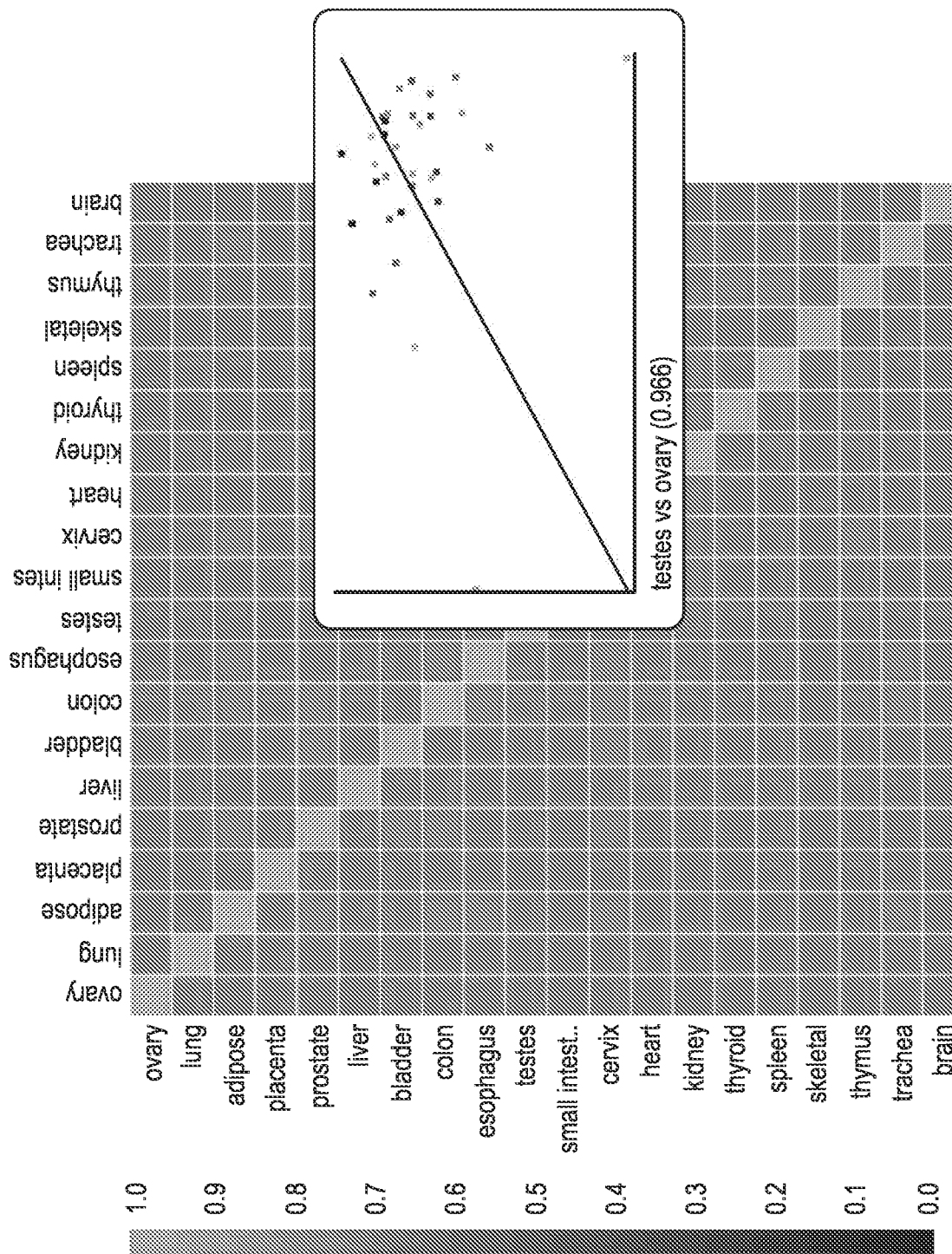
FIG. 9 illustrates an exemplary data visualization display for biological data according to various embodiments described herein.

In an analysis tab, the user can pull up, e.g., various visualization modules to view information related to the data. For example, as mentioned and as illustrated in FIG. 9, a heat map view can provide a color coded map of the data that can be used to see patterns. Selection of a certain cell within the heat map can then pull up further data such as the detailed plot as illustrated in FIG. 9. This can be used to cross check the data as discussed below.

Another visualization module that can be included on the analysis is the volcano plot module, which can show a volcano plot of the data. This data can show targets with expression above a certain target. Again, if the user wants to confirm the data, they can select one of the targets and pull up the Ct data to confirm.

Another visualization module can show correlation plots of the data. Again, if there are targets that stick out, the user can select a group of them and pull up data related to those targets. Or select one and get the amplification plot.

Figure 3:
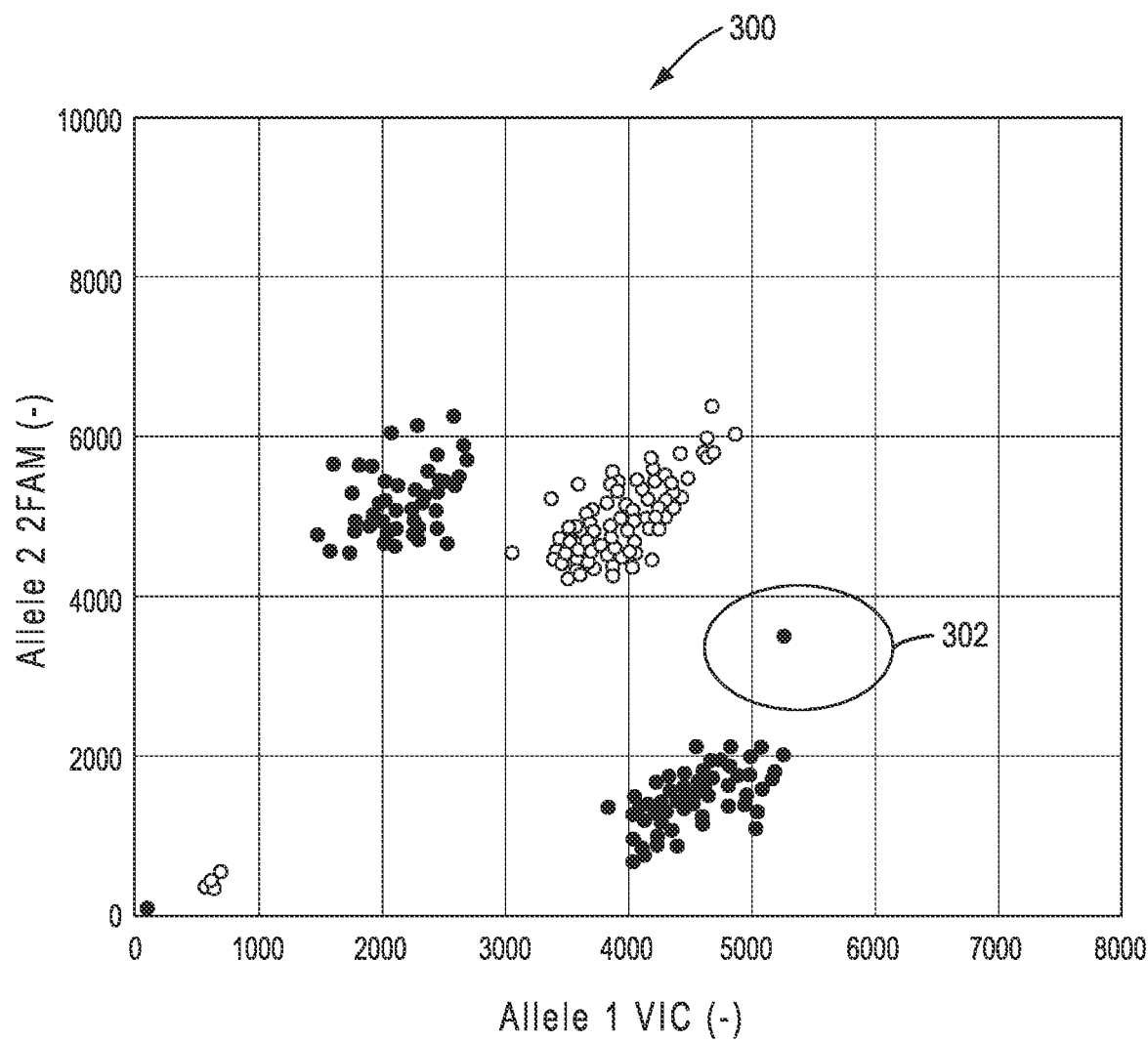
FIG. 3 illustrates another example of comparing types of biological data according to various embodiments described herein.

Thus, the user can constantly drill down or pull up further data to check the analysis. This ability to drill down and check data is illustrated with respect to FIG. 3, which illustrates a data visualization of a type of biological data. In this example, a copy number variation (CNV) assay performed on a sample can generate the data shown in data plot 300. According to various embodiments, a user is able to query other results you for this particular sample and covering the same sequence. For example, a CNV result may confirm whether a sample has CNV at the locus interrogated by the SNP assay.

Data point 302 illustrates a point a user may want to query further because of the zone it falls into on data plot 300. Data point 302 may have fallen into this zone because of copy number variation. For example, the person from whom the sample was obtained may have multiple copies of this gene and the number of the copies that are heterozygote is lower than the number of copies that are homozygote for allele 1. This could render it slightly responsive for allele 2 and mostly responsive of allele 1 (as in FIG. 3)—and not sit with the heterozygote cluster. Another reason data point 302 may be separate from the other groupings shown in data plot 300 is that the sample is bad or damaged, leading to an inadequate signal.

Further, a user may want to query data points where a sequencing result may exist to confirm whether a sample has the SNP at an interrogated location. Similarly, using embodiments of the methods and systems described herein, a user can also select to view and compare gene expression results for the same sample shown in data plot 300.

As can be seen in FIG. 1A, data from the different data files are presented and arranged in graphical representations based on the user graphical and/or textual tools. The graphical representations can include searching, gathering, arranging, and highlighting data in the plurality of data files based on corresponding characteristics, such as the same sample, gene, disease, or condition, for example. In various embodiments, a drag-and-drop function can allow a user to select desired file types and drag the file to an active area of user interface 120 for combining data to review and compare to generate a result.

In other embodiments, a user may store a workflow for a given sample. For example, a user may generate an allelic discrimination plot. For each sample, a query can be performed to get real time run results to ascertain sample quality. A user can record and apply steps of analysis to one or more groups of samples. And then ask for a statistical comparison of results at the end of those steps. These types of workflows can also be saved and used again in the future.

For example, a user may want to compare genotyping data to the underlying amplification data. The user may view a genotyping scatter plot on user interface 120 and select a point on the scatter plot. The underlying amplification data of the point may then be displayed to the user.

Figure 1B:
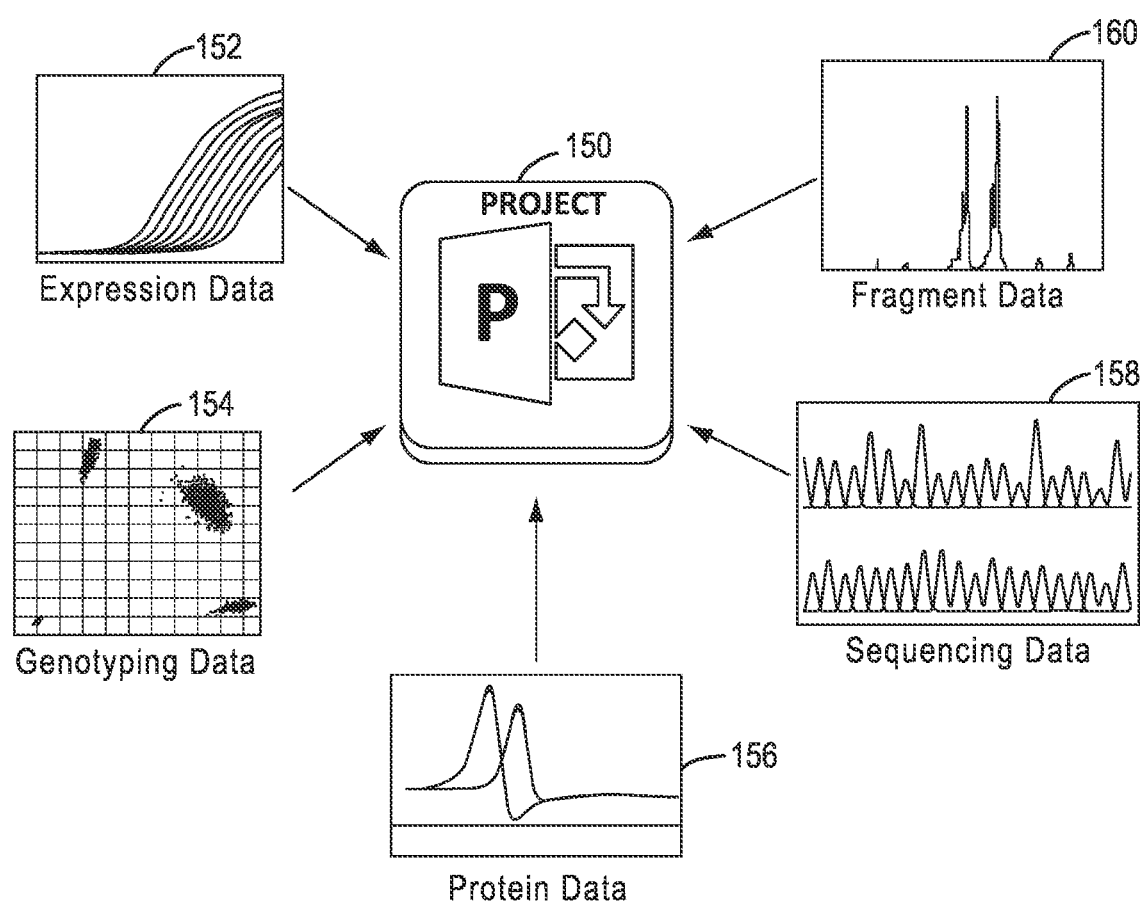
FIG. 1B illustrates an exemplary system according to various embodiments described herein.

FIG. 1B illustrates a representation of a workspace or project that can be created within system 600 according to an example embodiment and in accordance with the previous description. FIG. 1B graphically illustrates that various types of data and visualizations can all be incorporated into a single workspace or project 150. In the example shown in FIG. 1B, project 150 can receive expression data files 152, genotyping data files 154, protein data files 156, fragment data files 160, and sequencing data files 158. The plurality a biological data types may be viewed and further analyzed as described above.

Figure 4A:
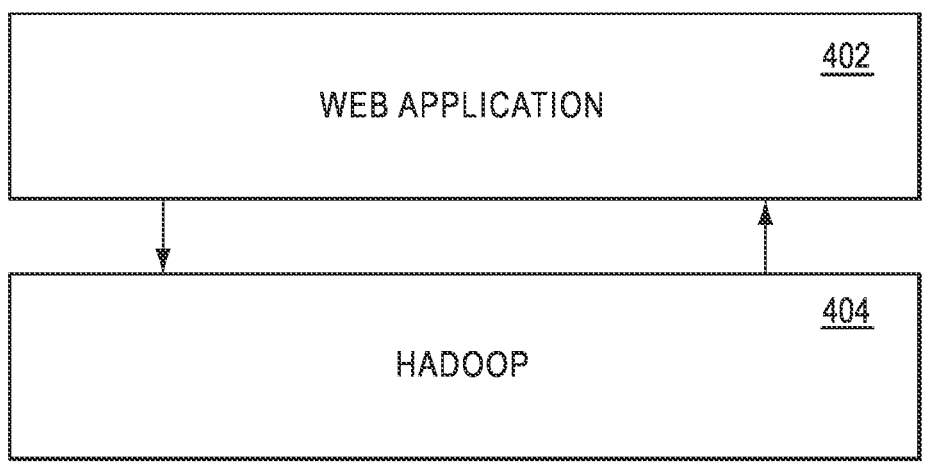
FIG. 4A illustrates a block diagram of a system for implementing various embodiments of described herein.
Figure 4B:
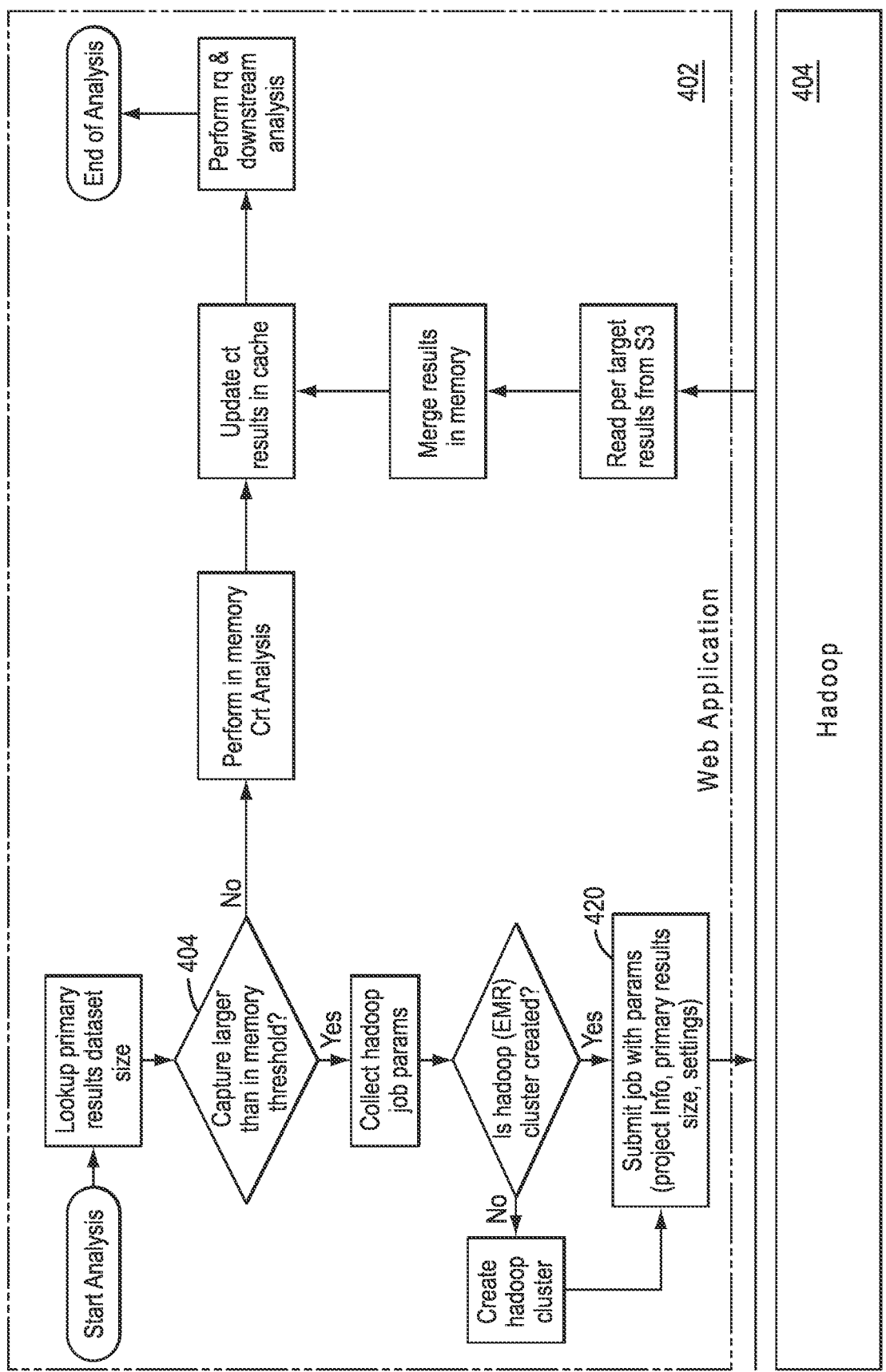
FIG. 4B illustrates the web application portion of the system of FIG. 4A for implementing various embodiments of described herein.
Figure 4C:
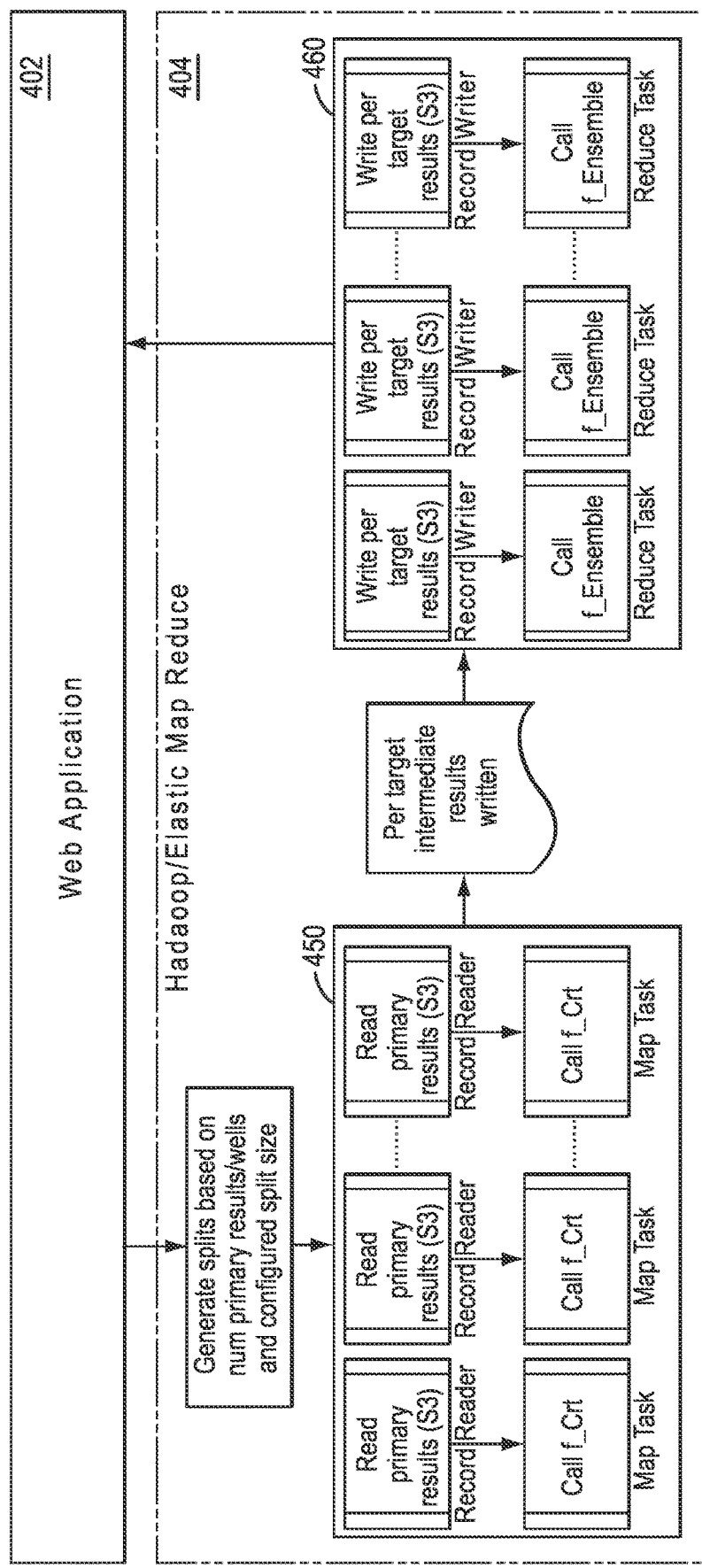
FIG. 4C illustrates the Hadoop portion of the system of FIG. 4A for implementing various embodiments of described herein.

FIGS. 4A-4C illustrate block diagrams of a system to enabling fast computation of various types of biological data using parallelization infrastructure in, e.g., system 600 and in accordance with one example embodiment. FIG. 4A shows communication between web application 402 that can be configured, e.g., for the visualization, analysis or manipulation of data sets within system 600, and Hadoop 404. A Hadoop is a software framework for distributed storage and distributed processing of Big Data on clusters of commodity hardware. A Hadoop comprises a Distributed File System (HDFS) configured to split files into large blocks (default 64 MB or 128 MB) and distribute the blocks among nodes in the cluster. For processing the data, the Hadoop Map/Reduce ships code (specifically Jar files) to the nodes that have the required data, and the nodes then process the data in parallel. This approach leverages data locality, in contrast to conventional HPC architecture which usually relies on a parallel file system (compute and data separated, but connected with high-speed networking).

FIGS. 4B and C are flow diagrams that illustrate the performance of the architecture of FIG. 4A in terms of performing a Crt calculation. As can be seen in FIG. 4B, when an analysis is triggered, the processor-executable instructions of web application 402 determine if the dataset size necessitates a Hadoop based execution of the analysis versus an in-memory execution in step 404. If so, Hadoop job parameters are collected in step 406, such as number, size and configuration of instances where the job will be run, location of files on, e.g., a cloud infrastructure, etc. In step 408, it is determined whether a corresponding Hadoop cluster has be created, and if so then the parameters are submitted to the Hadoop system 404 in step 420. If not, then the cluster is created in step 410 and the parameters are then provided in step 420.

If it is determined in step 404 that in-memory execution is sufficient, then the in-memory processing is carried out at step 412, which can cause various results or outputs to be updated in step 414. These results can then be forwarded for any downstream analysis in step 416.

With reference to FIG. 4C, when a Hadoop job is started, wherein the "map function" executes the compute intensive parts of the CRT calculation algorithm, per plate by target. As this step completes, several "reducer functions" gathers the results from the various map functions, as shown in 450. Each reducer function can get results from map functions with the same key. This allows the correct set of data (by target and plate) to be collected together. These results are stored in the Amazon storage (S3) 460. Downstream combinator services read the results computed, merge and send it back to web application 402, which can read the results in step 418 and merge the results in step 420.

The data parallelization executed allows fast execution of the CRT calculation, depending upon hardware configuration chosen for the execution. It should be noted; however, access from client devices 602, 612, and 630 to the database 650 to fetch data can be slow. Access to local memory is much faster. Accordingly, in certain embodiments, system 600 can be configured to pre-load data to a cache in order to optimize the user experience. In other embodiments, frequently accessed information can even be pre-computed and stored in the cache. Such pre-computed information can also be updated in the background to reflect changes in the database 650 as users interact with it.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the invention.

Figure 5:
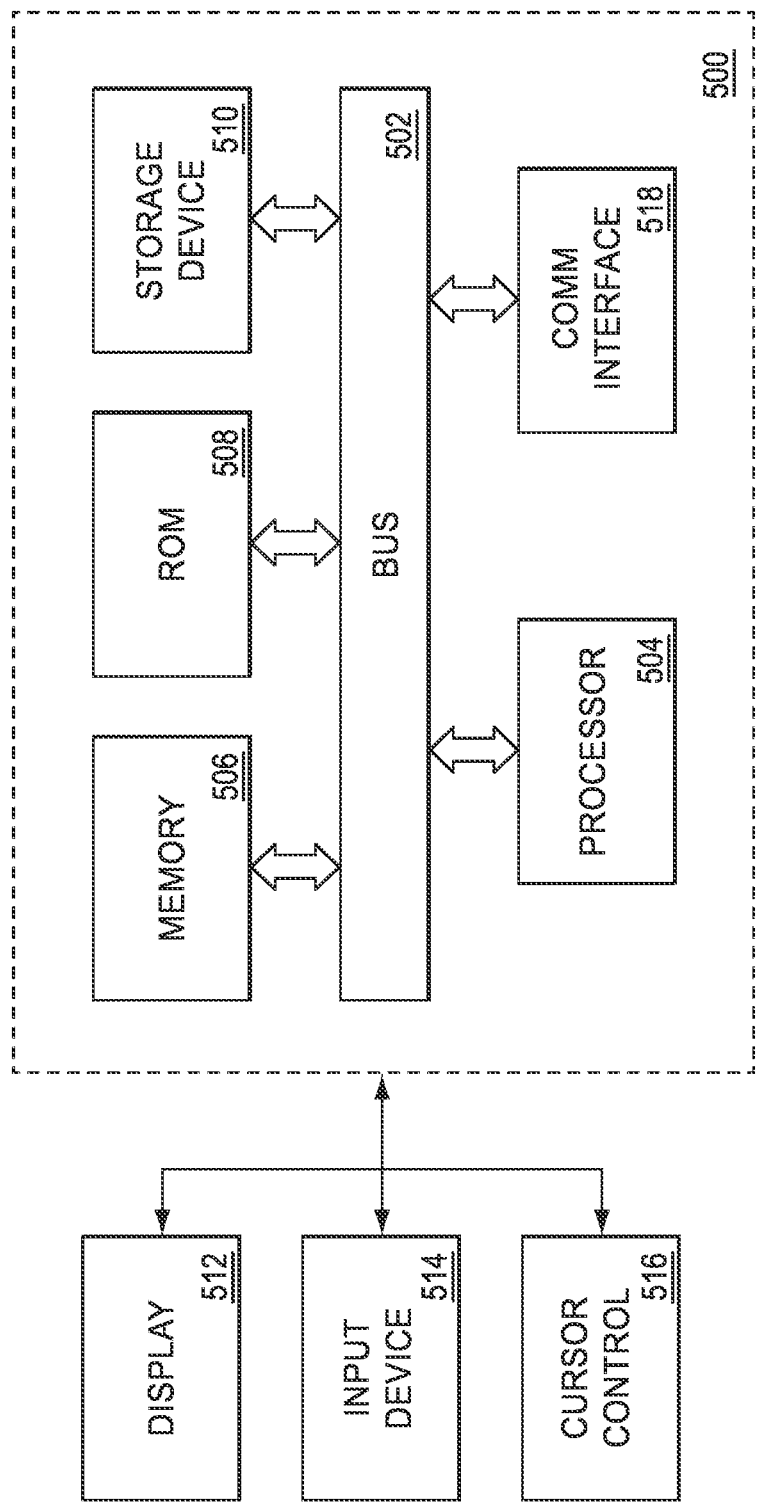
FIG. 5 illustrates an exemplary computing system for implementing various embodiments described herein.

FIG. 5 is a block diagram that illustrates a computer system 500 that can be employed to carry out processing functionality, and to implement various components or subsystems of the systems described herein according to various embodiments. For example, system 500 can comprise all or apportion of devices 640, client devices, 602, 612, or 630, servers 622, etc. Computing system 500 can include one or more processors, such as a processor 504. Processor 504 can be implemented using a general or special purpose processing engine such as, for example, a microprocessor, controller or other control logic. In this example, processor 504 is connected to a bus 502 or other communication medium.

Further, it should be appreciated that a computing system 500 of FIG. 5 can be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 500 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 500 may be configured to connect to one or more servers in a distributed network. Computing system 500 may receive information or updates from the distributed network. Computing system 500 may also transmit information to be stored within the distributed network that may be accessed by other clients connected to the distributed network.

Computing system 500 may include bus 502 or other communication mechanism for communicating information, and processor 504 coupled with bus 502 for processing information.

Computing system 500 also includes a memory 506, which can be a random access memory (RAM) or other dynamic memory, coupled to bus 502 for storing instructions to be executed by processor 504. Memory 506 also may be used for storing temporary variables or other intermediate information during execution of instructions to be executed by processor 504. Computing system 500 further includes a read only memory (ROM) 508 or other static storage device coupled to bus 502 for storing static information and instructions for processor 504.

Computing system 500 may also include a storage device 510, such as a magnetic disk, optical disk, or solid state drive (SSD) is provided and coupled to bus 502 for storing information and instructions. Storage device 510 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 510 may include other similar instrumentalities for allowing computer programs or other instructions or data to be loaded into computing system 500. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 510 to computing system 500.

Computing system 500 can also include a communications interface 518. Communications interface 518 can be used to allow software and data to be transferred between computing system 500 and external devices. Examples of communications interface 518 can include a modem, a network interface (such as an Ethernet or other NIC card), a communications port (such as for example, a USB port, a RS-232C serial port), a PCMCIA slot and card, Bluetooth, etc. Software and data transferred via communications interface 518 are in the form of signals which can be electronic, electromagnetic, and optical or other signals capable of being received by communications interface 518. These signals may be transmitted and received by communications interface 518 via a channel such as a wireless medium, wire or cable, fiber optics, or other communications medium. Some examples of a channel include a phone line, a cellular phone link, an RF link, a network interface, a local or wide area network, and other communications channels.

Computing system 500 may be coupled via bus 502 to a display 512, such as a cathode ray tube (CRT) or liquid crystal display (LCD), for displaying information to a computer user. An input device 514, including alphanumeric and other keys, is coupled to bus 502 for communicating information and command selections to processor 504, for example. An input device may also be a display, such as an LCD display, configured with touchscreen input capabilities. Another type of user input device is cursor control 516, such as a mouse, a trackball or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane. A computing system 500 provides data processing and provides a level of confidence for such data. Consistent with certain implementations of embodiments of the present teachings, data processing and confidence values are provided by computing system 500 in response to processor 504 executing one or more sequences of one or more instructions contained in memory 506. Such instructions may be read into memory 506 from another computer-readable medium, such as storage device 510. Execution of the sequences of instructions contained in memory 506 causes processor 504 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 504 for execution. Such instructions, generally referred to as "computer program code" (which may be grouped in the form of computer programs or other groupings), when executed, enable the computing system 500 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 510. Volatile media includes dynamic memory, such as memory 506. Transmission media includes coaxial cables, copper wire, and fiber optics, including the wires that comprise bus 502.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on magnetic disk of a remote computer. The remote computer can load the instructions into its dynamic memory and send the instructions over a telephone line using a modem. A modem local to computing system 500 can receive the data on the telephone line and use an infra-red transmitter to convert the data to an infra-red signal. An infra-red detector coupled to bus 502 can receive the data carried in the infra-red signal and place the data on bus 502. Bus 502 carries the data to memory 506, from which processor 504 retrieves and executes the instructions. The instructions received by memory 506 may optionally be stored on storage device 510 either before or after execution by processor 504.

It will be appreciated that, for clarity purposes, the above description has described embodiments with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Figure 2:
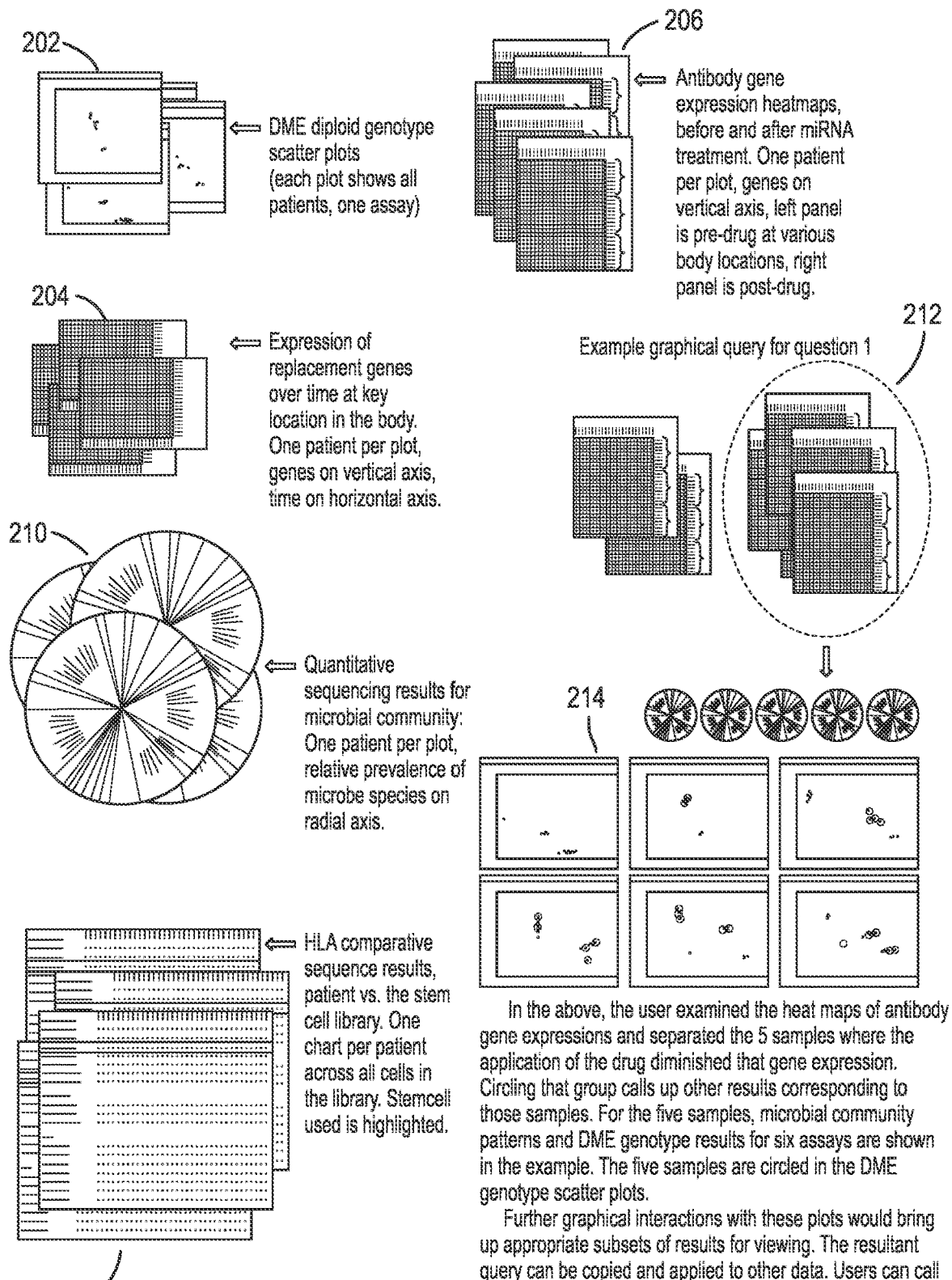
FIG. 2 illustrates an example of comparing types of biological data according to various embodiments described herein.

FIG. 2 illustrates an example of comparing types of biological data according to various embodiments described herein. In this example, a user is investigating a stem cell therapy for a genetic disorder of the liver and a micro-RNA treatment that can inhibit the expression of an immune response to a slight HLA mismatch between the stem cell and the patient. The correct stem cell population must be chosen for the patient. To accomplish this, sequencing of the patient's HLA genes is needed to determine the HLA type to avoid a strong immune response against the introduced stem cells. A drug can then be selected to neutralize antibodies that can attack the stem cells. The effectiveness of the drug can be determined by checking drug metabolizing genetic profile and the genetic profile of gastrointestinal flora and the amount of antibodies harmful to the introduced stem cells. To monitor the effectiveness of the stem cell introduction, gene expression of the introduced genes is measured to determine their penetration into the relevant organs. In summary, the workflow may be as follows:

1. Sequence HLA genes to identify match between stem cell and patient;
2. DME genotyping to check drug efficacy;
3. Population sequencing of intestinal flora to check drug efficacy;
4. Monitor gene expression levels for antibodies of interest; and
5. Look at gene expression of introduced genes to monitor penetration of gene therapy.

As noted above, in certain embodiments this workflow can be defined within the workspace, e.g., through the dashboard, which can then guide the user to obtain or search for all of the relevant data to perform the analysis.

The data obtained in step 1 above can be graphically displayed, e.g., within project 150, as illustrated by the graphical representations 208 in FIG. 2. These graphical representations illustrate the HLA comparative sequence results for the patient against the stem cell library. One chart can be presented per patient across all cells in the library. The stem cell used can be highlighted. The scatter plots 202 in FIG. 2 represent the DME diploid genotypes obtained in step 2 above. The plots 210 illustrate the quantitative sequencing results for a microbial community in step 3, where each plot is one patient and the relative prevalence of the microbe species is illustrated on the radial axis. The antibody gene expression heat maps 206 for before and after miRNA treatment correspond to step 4. Each map corresponds to one patient and genes are displayed on the vertical axis. The left panel of each map is the pre-drug data at various body locations; the right panel is post drug. The plots 204 illustrate the expression of replacement genes over time at key locations in the body according to step 5. Each plot corresponds to one patient, with genes on the vertical access and time on the horizontal axis.

There are several types of biological analysis applications that produce the types of biological data illustrated in FIG. 2. For example, the following biological analysis applications may be used in this example:

1. A genotyping application that generates bi-allelic scatter plots of the DME genes (202)
2. A gene expression application that generates patient-specific heatmaps of relative expression levels (with respect to an appropriate reference gene) of the introduced genes vs. time at the location in the body where expression is expected to be high at the sampling times (204)
3. A gene expression application that generates patient-specific heatmaps of relative expression levels for the genes associated with the targeted antibodies at various sampling times following introduction of the stemcells without and with the drug (206)
4. A sequencing application that produces diploid sequences for the HLA genes (208)
5. A sequencing application that produces mixed base sequences (population sequences) for the microbial flora samples) (210)

Once the results of the various steps in the workflow are obtained, as illustrated in FIG. 2, then the user may have the following questions:

1. Are there patterns of DME genotypes and microbial population genetic sequences that are associated with greater effectiveness of neutralizing antibodies?
2. Of the people with high target-antibody counts (gene expression), what were the DME/microbial profiles for those where the gene therapy failed/succeeded?
3. Is there a certain subset of antibodies for which a high gene expression is particularly damaging to the therapy?
4. Are there particular mixtures of microbial flora that help/hinder the effectiveness of the drug in suppressing the target antibodies?
5. How close must the HLA match be for therapy to succeed?

It can be appreciated that once the results are gathered, organized, annotated, etc., in a single workspace as illustrated in FIG. 2, answering such questions, e.g., by further analysis, cross referencing, and assessment of the data is made much easier than in conventional systems. For example, a user can now perform a graphical query, illustrated in 212, to visually select one or more data points from a graphical display. In other words, the user may select, by using the user interface, data points which the user would like more information about. The attributes of those data points such as sample name, target name, target sequence, tags, which are common across the data sets, can then be used for querying one or more sources of information present either in the form of different types of results across applications, or searching biological information databases.

FIG. 11 illustrates yet another example of comparing a plurality of biological data types according to various embodiments described herein. In this example, cell data for mice is compared to that of humans to see if there is a correlation in terms of what miRNA's are affected when there is an exposure to high levels of alcohol. At the same time, SNP data can be analyzed to identify promoter regions that could influence miRNA expression related to alcoholism. Quality control can also be performed by looking at Crt and other data, all within the common workspace.

The systems and methods described herein can also allow a user to perform complex searches or queries across the data in database 650. This can be accomplished by indexing or tagging all of the information, content, attributes, etc., of the data and then creating a non-relational data base from these indexes or tags. Thus, the user can search the data by any such tags. Moreover, the user can build associations between the data based on the tags and use these associations to create groups, projects, etc.

In certain embodiments, system 600 can include a machine learning engine (not shown) that can automatically search the tags, detect associations, patterns, relationships, etc., which may not otherwise be noticeable extending the power of system 600 even further.

System 600 can also enable unique visualizations of the various data sets. For example, FIG. 7 illustrates an exemplary graphical representation display according to one example embodiment. The example in FIG. 7 can be termed a flower plot visualization 700. The flower plot 700 provides an alternate way of visualizing amplification curves. In certain embodiments, a synced display of a flower plot 700 can be presented side by side with the traditional representation of amplification curves 701 as illustrated in FIG. 7. This allows user to quickly determine quality of data of a large number of amplification curves by allowing efficient navigation/selection along multiple attribute vectors.

For example, the radius 704 of a flower plot visualization 700 can represent the fluorescence scale. Each well (or data point) can be assigned a unique angle (a). The change in Rn value from each cycle is plotted using a different color (from a sequential color scale). For example, with reference to FIG. 7, the Rn change in cycle 0 to 1, is plotted in the deepest blue (indicated by 702) from center of the circle outward (along a particular angle corresponding the position of the well). Well position on the circle can be determined by various "attributes": In the example of FIG. 7, it is arranged by well location on plate. Thus slice "A" has all wells from row A of the plate. Slices can thus be mapped to attributes such as samples or assays.

Samples that had earlier amplification should have most of the "petals" displayed, e.g., in blue/green colors (as the lengths will have the early cycle colors). Samples where amplification took place in later cycles should have most of the "petals" displayed in, e.g., orange/red colors (as the lengths will have the late cycle colors). Wells where no amplification took place should have small petals. Wells that started at an abnormal high level should have petals starting mid-way (not at center).

A user can then select certain wells from the flower plot 700. In response, the corresponding wells on the traditional view of the amplification plot 701 are selected, e.g., highlighted in the display to the user. Conversely, if a user selects certain wells from the traditional amplification plot 701, the corresponding wells on the flower plot 700 can be, e.g., highlighted on the display to the user.

Depending on the embodiment, the flower plot 700 can be arranged by following "attributes": targets, samples, plate location (view in screenshot), sort by amp score/confidence/Cq, task. The color scheme for the amp plot can be user selectable: monochromatic versus color palette.

In certain embodiments, a movable line 705 on the amplification curves 701—which acts as a Cycle threshold—should have a corresponding "ring" 706 moving in a synchronized fashion on the flower plot 700. This allows user to see how a threshold is impacting all of his wells.

In certain embodiments, the user can be allowed to choose between a plurality of color schemes for the visual and should be able to add labels to the flower plot 700. These labels can also show up in the corresponding tradition amplification plot. Moreover, the label can be stored or associated with the underlying data and may be used by other applications or visualization engines.

In embodiments used for numerical sorts (such as Ct, end point or amp score), the perimeter of the flower pot can be used as a continuous scale and label the section separation lines as grid lines on that scale. For alpha-numeric sorts (Such as by sample, row/column positions or targets), each section can be labeled only when #sections <X. Further, the data can be ordered by options to include, e.g., Ct, amp-score, end point, column/row positions, and frequency of flags. In certain embodiments, if #sections >X, then the spokes/petals can be shown in 4 quadrants with no section labeling. Drill downs into each quadrant can be enabled in order to make a new amp-wheel. A mechanism can also be provided to go back to the previous drill-down level. The table of data associated with the plot should only show the active set of wells on the amp wheel.

Figure 8:
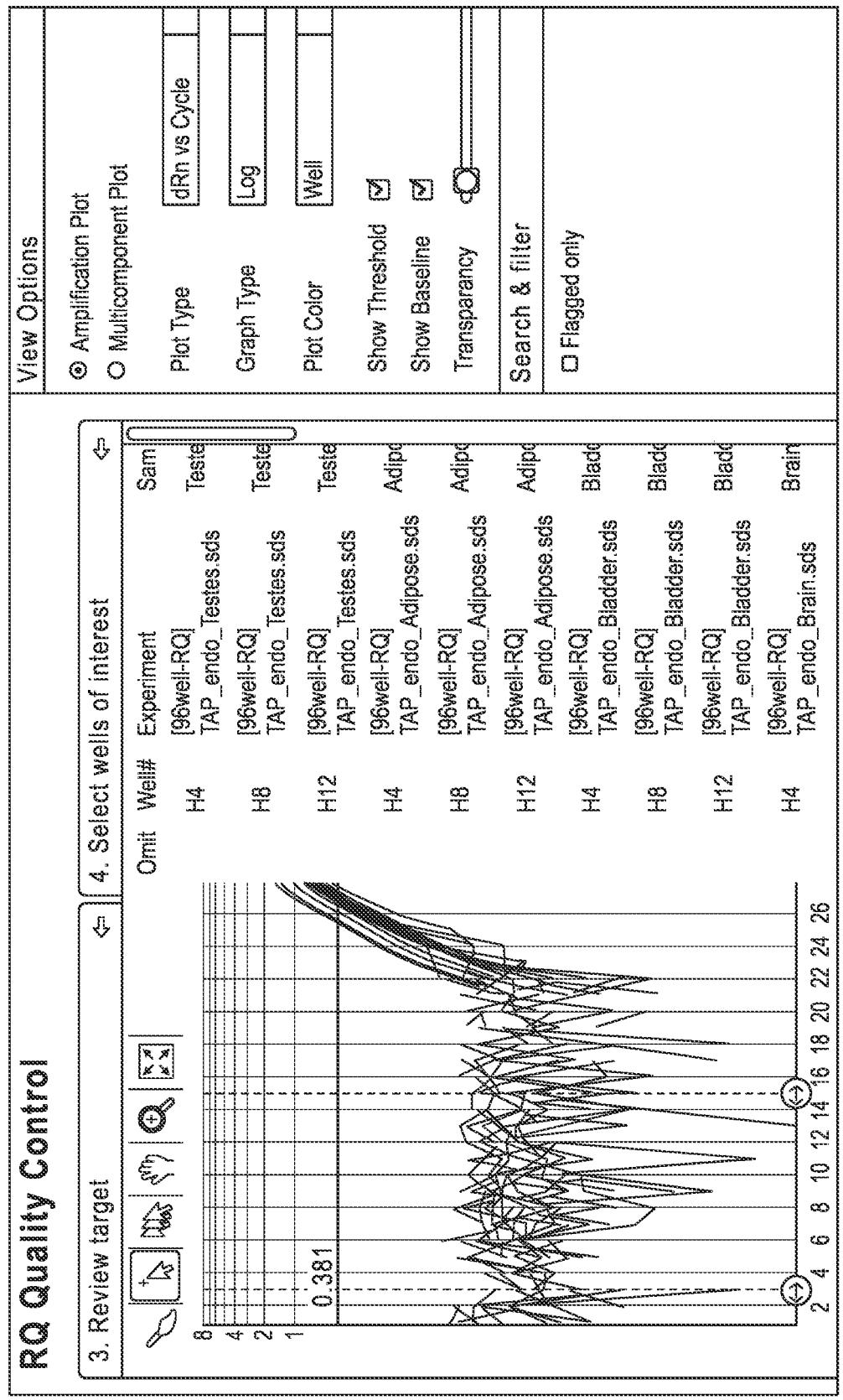
FIG. 8 illustrates an exemplary data visualization display for biological data according to various embodiments described herein.

As another example of the unique visualizations that can be provided, FIG. 8 illustrates using transparency data plots, according to various embodiments, to allow a user to estimate density of points for the allelic discrimination/cluster plots. By using different levels of transparency over a plot, over plotted regions will be at deeper shade than the non-over plotted regions. This assists a user in getting a sense of the density/distribution of the data. A user may also adjust the transparency levels by toolbars displayed to the user on the user interface.

As another example, FIG. 9 illustrates an interactive heat map that can be presented to the user to review and compare data according to various embodiments. In this example visualization, selection can be driven by the branch of a dendogram (for the top level selection—instead of by rows from the left bottom). A tag can be overlaid on the dendogram order to determine information such as: Do smokers cluster together? Order by tags can then be enabled. Other ordering techniques can include ordering by gene ordering of one bio group. This can enable determinations, such as: if normal has X gene most expressed, what is other groups doing for that gene?

In certain embodiments, selection of an area on the heat map will cause the application to navigate to "amplification curves by target" plot, or if samples are selected to "amplification curves by sample" plot. Non-contiguous zones can also be selected on, e.g., a volcano plot and this will cause the system to pull up the heat map, filtered by that selection.

Figure 10:
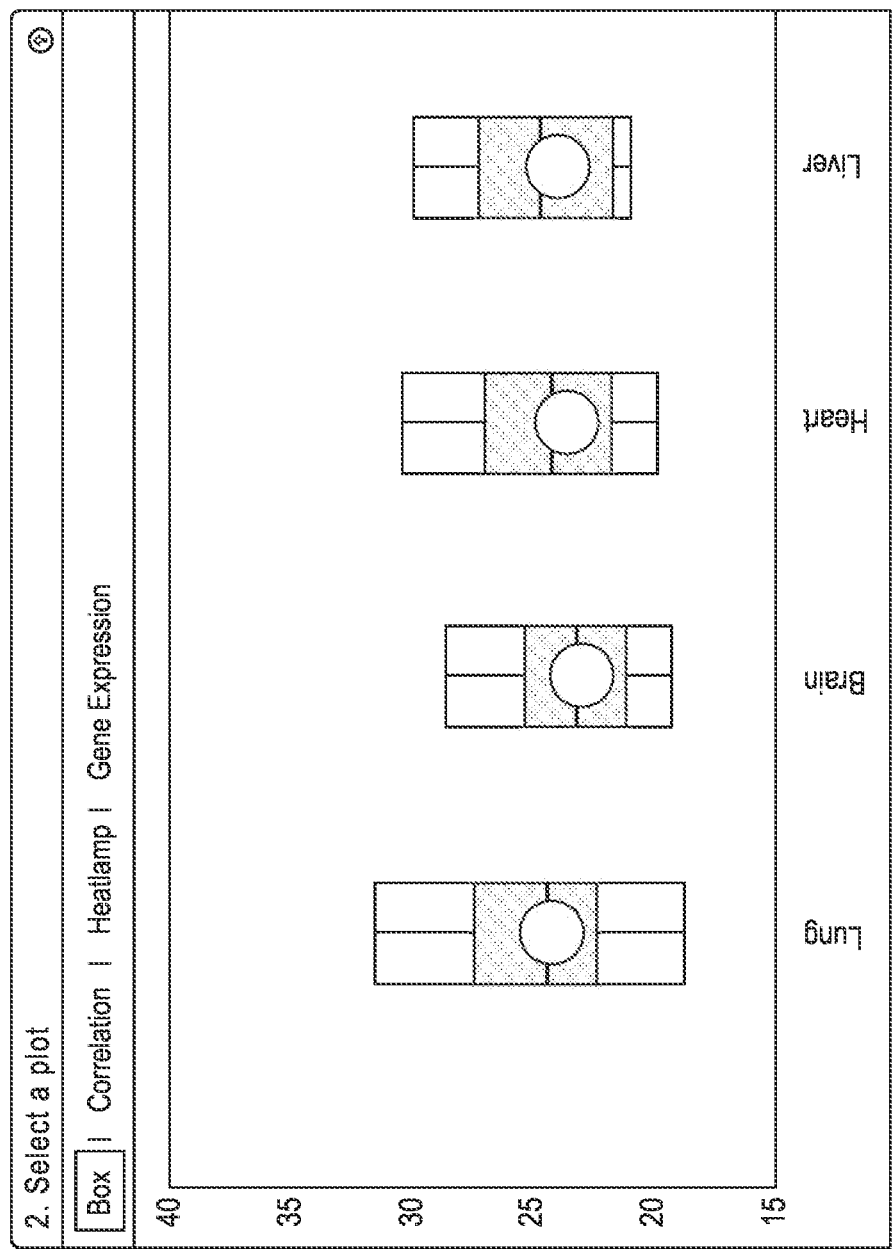
FIG. 10 illustrates an exemplary data visualization display for biological data according to various embodiments described herein.

FIG. 10 illustrates another exemplary data visualization display for biological data according to various embodiments described herein.

Although various embodiments have been described with respect to certain exemplary embodiments, examples, and applications, it will be apparent to those skilled in the art that various modifications and changes may be made without departing from the present teachings.

Appendix A shows the system that may implement the above.

What is claimed is:

1. A system for analyzing biological data, comprising:
    a storage configured to store information related to a plurality of data files containing biological data obtained from a plurality of biological analysis devices, wherein each data file includes output data from an application configured to analyze a technology vector applied to a biological molecule vector;
    a server configured to:
        host a plurality of applications in a dashboard, each of the plurality of applications configured to be implemented on the server and to provide analysis, manipulation, comparison, visualization, or a combination thereof, of the biological data included in the data files associated with different technology vectors,
        create tags associated with the information included in the plurality of data files and store the tags in the storage;
    a search engine configured to enable the tags to be searched and to build associations between the tags; and
    a display configured to provide a user interface including the dashboard with a first visualization associated with a first data file of the plurality of data files and a second visualization associated with a second data file of the plurality of data files, wherein the first and second data files are from two different applications, wherein the first and second data files are associated with respective first and second technology vectors of the different technology vectors applied to the same biological molecule vector,
    wherein a first tag is associated with information in the first data file and a second tag is associated with information in the second data file, the second tag being associated with the first tag, and wherein manipulation of the first tag affects the second tag such that both the first visualization associated with the first data file and the second visualization associated with the second data file are changed.

2. The system of claim 1, wherein the server is further configured to associate at least some of the plurality of applications with certain data files based on the tags.

3. The system of claim 1, wherein the dashboard is configured to display information related to the data files and the plurality of applications, and to allow users to create projects consisting of several of the plurality of data files and launch applications related to those data files.

4. The system of claim 1, wherein the technological vectors include at least one of CE sequencing, NGS sequencing, qPCR, dPCR, melt, microArrays, and combinations thereof.

5. The system of claim 1, wherein the biological molecule vectors include at least one of DNA, RNA, proteins, and miRNA.

6. The system of claim 1, wherein the applications that produce output data include at least one of: genotyping applications, gene expression applications, absolute quantification applications, Copy Number Variation (CNV) analysis applications, Single Nucleotide Polymorphism (SNP)

array analysis applications, High Resolution Melt (HRM) analysis applications, and presence-absence analysis applications.

7. The system of claim 1, wherein the biological data includes data from a plurality of experiments.

8. The system of claim 1, wherein the plurality of applications includes at least one of: visualization modules, analysis modules, and quality control modules, and wherein the modules are linked with the data based on the tags enabling a user to drill down through the data in the data files or move from one module to the next and review information related to the same data or data files within the different modules.

9. The system of claim 1, wherein different visualizations of the same data or related data can be displayed to a user within the same screen.

10. The system of claim 1, wherein the plurality of applications allow a user to analyze the data files concurrently and compare information or analysis for the data file produced by different applications.

11. A system for analyzing biological data, comprising:
a storage configured to store a plurality of data files containing biological data obtained from a plurality of biological analysis devices, wherein each data file includes output data from an application configured to analyze a technology vector applied to a biological molecule vector;
a server configured to:
create tags associated with information included in the plurality of data files and store the tags in the storage, and
host a plurality of applications in a dashboard, wherein at least some of the plurality of applications includes at least one of: visualization modules, analysis modules, and quality control modules, and wherein the modules are linked with the data based on the tags enabling a user to drill down through the data in the data files or move from one module to the next and review information related to the same data or data files within the different modules; and
a display configured to provide a user interface including the dashboard with a first visualization associated with a first data file of the plurality of data files and a second visualization associated with a second data file of the plurality of data files, wherein the first and second data files are from two different applications, wherein the first and second data files are associated with respective first and second technology vectors of the different technology vectors applied to the same biological molecule vector,
wherein a first tag is associated with information in the first data file and a second tag is associated with information in the second data file, the second tag being associated with the first tag, and wherein manipulation of the first tag affects the second tag such that both the first visualization associated with the first data file and the second visualization associated with the second data file are changed.

12. The system of claim 11, wherein the dashboard is configured to display information related to the data files and the plurality of applications, and to allow users to create projects, launch application, and collaborate with other users.

13. The system of claim 11, wherein different visualizations of the same data or related data can be displayed to a user with in the same screen.

14. The system of claim 11, wherein at least one of the applications is configured to create a radial view of a plurality of traditional amplification curves representing a corresponding fluorescence scale, and wherein each data point represented in the data can be assigned a unique angle in the radial view.

15. The system of claim 14, wherein changes in Rn value from each cycle can be plotted using a different color (from a sequential color scale).

16. The system of claim 14, wherein each data point position of the radial view is determined based on one or more attributes.

17. The system of claim 16, wherein the attributes include at least one of: a target, a sample, a plate location, amplification score, confidence, Cq, and task.

18. The system of claim 14, wherein the radial view can be interconnected with traditional representation of the amplification curves such that selection of a data point in the radial view will cause the same data point to be highlighted in the corresponding traditional amplification curves.

19. The system of claim 18, wherein the radial view and the traditional amplification curves can be displayed together.

* * * * *